US008986395B2

(12) United States Patent
McLeary

(10) Patent No.: US 8,986,395 B2
(45) Date of Patent: Mar. 24, 2015

(54) HAND PROSTHESIS

(75) Inventor: Gordon McLeary, Lochwinnoch (GB)

(73) Assignee: Touch EMAS Limited, Livingston (GB)

( * ) Notice: Subject to any disclaimer, the term of this patent is extended or adjusted under 35 U.S.C. 154(b) by 95 days.

(21) Appl. No.: 13/580,303

(22) PCT Filed: Feb. 24, 2011

(86) PCT No.: PCT/GB2011/050368
§ 371 (c)(1),
(2), (4) Date: Oct. 31, 2012

(87) PCT Pub. No.: WO2011/107778
PCT Pub. Date: Sep. 9, 2011

(65) Prior Publication Data
US 2013/0046395 A1 Feb. 21, 2013

(30) Foreign Application Priority Data

Mar. 4, 2010 (GB) .................. 1003573.1

(51) Int. Cl.
A61F 2/54 (2006.01)
A61F 2/58 (2006.01)
A61F 2/68 (2006.01)
B25J 15/00 (2006.01)
(Continued)

(52) U.S. Cl.
CPC .......... A61F 2/583 (2013.01); A61F 2002/6836 (2013.01); B25J 15/0009 (2013.01); A61F 2/586 (2013.01); A61F 2002/587 (2013.01); A61F 2002/701 (2013.01); A61F 2002/704 (2013.01); A61F 2002/7625 (2013.01)
USPC ............................................. 623/24; 623/64

(58) Field of Classification Search
CPC ....................... A61F 2002/587; B25J 15/0009
USPC ........................................................ 623/24
See application file for complete search history.

(56) References Cited

U.S. PATENT DOCUMENTS 2,669,727 A 2/1954 Opuszenski
4,955,918 A 9/1990 Lee
(Continued)

FOREIGN PATENT DOCUMENTS

CN 1803413 7/2006
JP 53-11456 * 2/1978 ...................... 623/24
(Continued)

OTHER PUBLICATIONS

Connolly, "Prosthetic hands from Touch Bionics," Industrial Robot, 2008, pp. 290-293, vol. 35, No. 4, Emerald Group Publishing Limited.
(Continued)

Primary Examiner — David H Willse
(74) Attorney, Agent, or Firm — K&L Gates LLP

(57) ABSTRACT

A hand prosthesis (15) including a hand chassis (15), a thumb member (22) mounted on the hand chassis for rotation of the thumb member in relation to the hand chassis about an axis extending generally along the length of the thumb member, a motor (64) disposed on one of the hand chassis and the thumb member, the motor being operable to drive a worm (56) and a worm gear wheel (54) disposed on the other of the hand chassis and the thumb member, the worm being in engagement with the worm gear wheel such that, upon operation of the motor, the thumb member rotates in relation to the hand chassis.

20 Claims, 6 Drawing Sheets

(51) Int. Cl.
*A61F 2/70* (2006.01)
*A61F 2/76* (2006.01)

(56) References Cited

U.S. PATENT DOCUMENTS

| | | | |
|---|---|---|---|
| 4,990,162 A | 2/1991 | LeBlanc et al. | |
| 5,888,246 A | 3/1999 | Gow | |
| 7,370,896 B2 * | 5/2008 | Anderson et al. | 294/106 |
| 2006/0158146 A1 | 7/2006 | Tadano | |
| 2008/0262634 A1 | 10/2008 | Puchhammer | |

FOREIGN PATENT DOCUMENTS

| | | | |
|---|---|---|---|
| WO | 9524875 | 9/1995 | |
| WO | 03017880 | 3/2003 | |
| WO | 2007063266 | 6/2007 | |
| WO | 2007076764 | 7/2007 | |
| WO | 2007076765 | 7/2007 | |
| WO | WO 2010/018358 A2 * | 2/2010 | A61F 2/58 |

OTHER PUBLICATIONS

PCT International Search Report and Written Opinion of International Searching Authority for International Patent Application No. PCT/GB2011/050368, mailed Jun. 21, 2011, 12 pages.

PCT International Preliminary Report on Patentability for International Patent Application No. PCT/GB2011/050368, mailed Sep. 13, 2012, 7 pages.

* cited by examiner

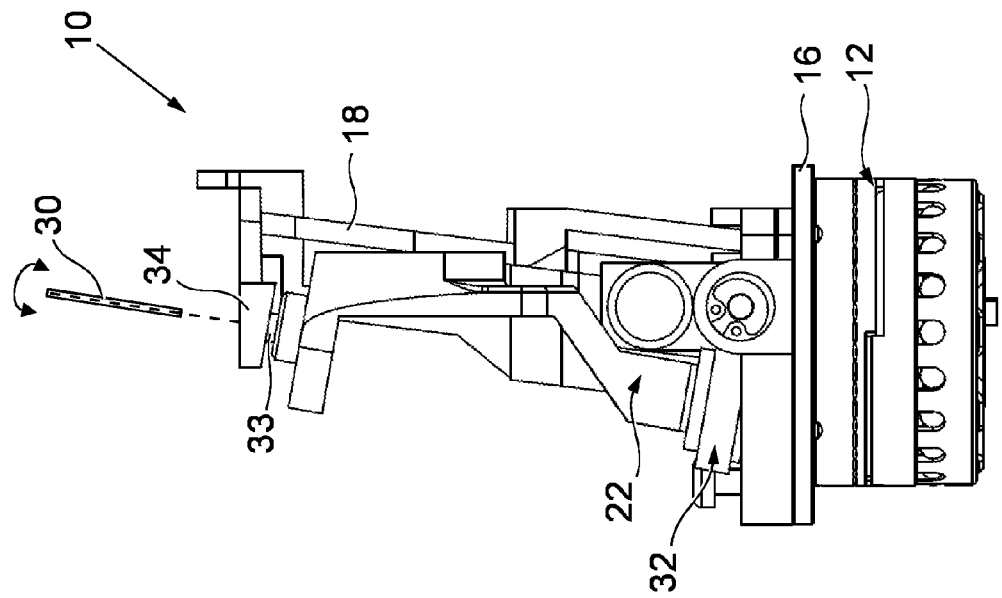
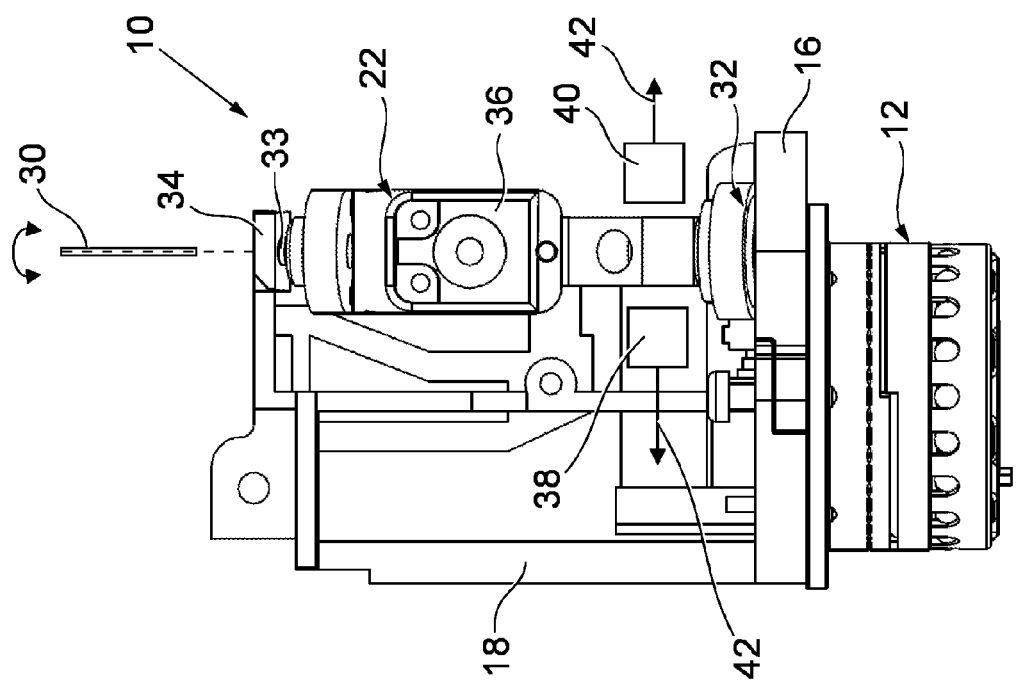

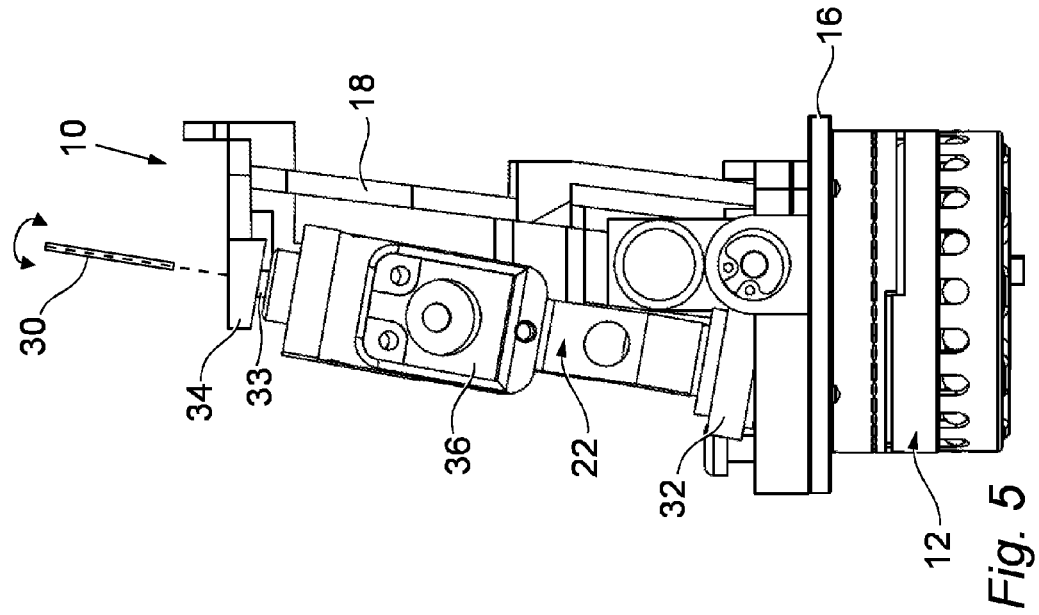
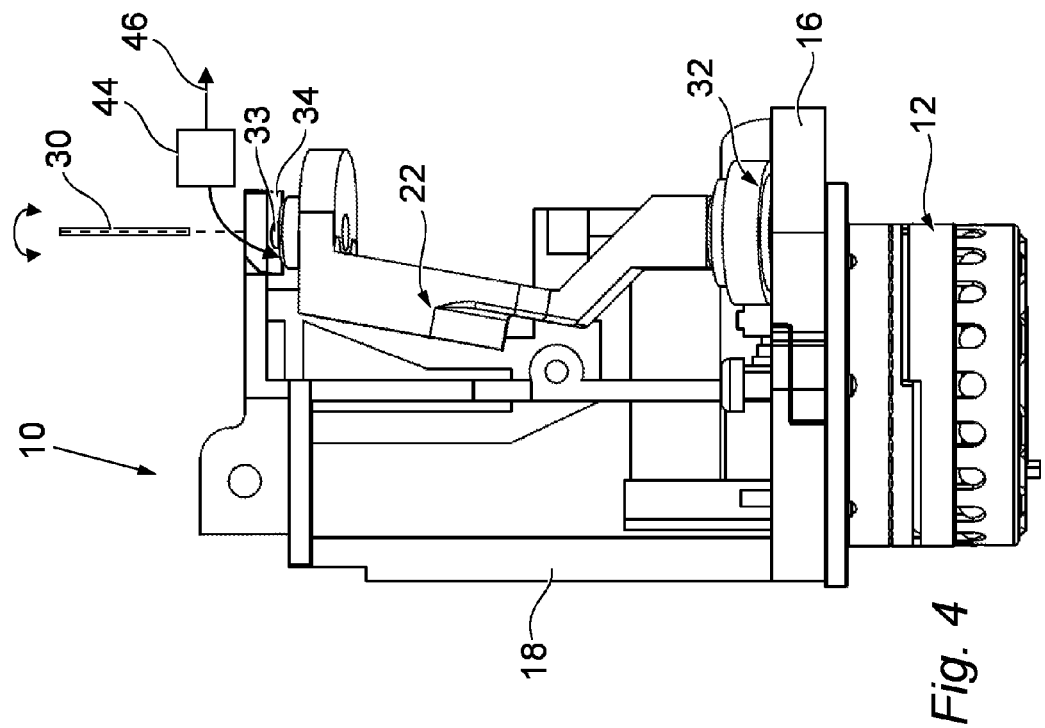

HAND PROSTHESIS

CROSS REFERENCE TO RELATED APPLICATIONS

This is the national phase under 35 U.S.C. §371 of International Application No. PCT/GB2011/050368, filed on Feb. 24, 2011, which claims priority to and the benefit of United Kingdom Patent Application No. 1003573.1, filed on Mar. 4, 2010, the entire disclosures of each of which are incorporated by reference herein.

FIELD OF THE INVENTION

The present invention relates to a hand prosthesis comprising a motor driven thumb member.

BACKGROUND TO THE INVENTION

Hand prostheses with motor driven digits are known. For example, U.S. Pat. No. 5,888,246 describes a motor drive system and linkage for a hand prosthesis. The hand prosthesis of U.S. Pat. No. 5,888,246 has at least one motor driven digit with the digit moving around an axis to thereby achieve flexion and extension.

The present inventor has appreciated known motor driven hand prostheses to have shortcomings.

According to an object for the present invention there is provided an improved hand prosthesis having at least one digit member and comprising a motor that is operative to move the at least one digit member.

STATEMENT OF INVENTION

The present invention has been devised in the light of the present inventor's appreciation of the shortcomings of known hand prostheses. Therefore, according to a first aspect of the present invention, there is provided a hand prosthesis comprising:

a hand chassis;
a thumb member mounted on the hand chassis for rotation of the thumb member in relation to the hand chassis about an axis extending generally along the length of the thumb member;
a motor disposed on one of the hand chassis and the thumb member, the motor being operable to drive a worm;
a worm gear wheel disposed on the other of the hand chassis and the thumb member, the worm being in engagement with the worm gear wheel such that, upon operation of the motor, the thumb member rotates in relation to the hand chassis.

In use, rotation of the thumb member in relation to the hand chassis about an axis extending generally along the length of the thumb member provides for movement of the thumb member in a fashion that approximates to the movement provided by the carpometacarpal joint of a natural thumb. Hence, movement of the thumb member of the hand prosthesis enables the position of the thumb member in relation to finger members of the prosthetic hand to be changed. For example, in a first position the thumb member may oppose an index finger member of the prosthetic hand and in a second position the thumb member may oppose a middle finger member of the prosthetic hand. In the position where the thumb member opposes the index finger, the hand prosthesis may perform a "pinching" action between the index finger and the thumb member (i.e. a two-digit pinch). In the position where the thumb member opposes the middle finger, the hand prosthesis may perform a pinching action between the middle finger and the thumb member. It is also possible that the thumb member may be positioned between the index finger and the middle finger. In this position, the hand prosthesis may perform a pinching action between the index finger, middle finger and thumb member (i.e. a three-digit pinch, or tri-pod pinch). The position of the thumb member may also be such that the thumb member is rotated away from the fingers, such that the hand prosthesis may perform a "palm grip" or "lateral gripping" action, where a flexion action of each of the fingers brings them towards the palm chassis (see below) to allow the hand prosthesis to grip an object between the fingers and the palm chassis. In the "palm grip" position, or when the fingers are at least part of the way toward the palm chassis, the thumb member may be brought from an initial position where it is rotated away from the fingers to a final position where it presses against one or more of the fingers (typically the index finger). This position is called the "lateral grip" or "key grip" position in which the thumb presses on the top of the side of the index finger, like holding a business card.

The configuration of worm and worm gear wheel may provide a drive mechanism that is more compact than prior art drive mechanisms. In addition, the configuration of worm and worm gear wheel may provide a drive mechanism that is capable of higher torque and a greater precision of movement than prior art drive mechanisms.

Alternatively or in addition, the thumb member may be rotatable about an axis extending substantially along the length of the thumb member.

Alternatively or in addition, the thumb member may be rotatable about a longitudinal axis of the thumb member.

Alternatively or in addition, the motor may be disposed on the hand chassis and the worm gear wheel may be disposed on the thumb member. The worm gear wheel may be disposed towards a proximal end of the thumb member. Disposing the motor on the hand chassis avoids disposing the motor in the normally limited space provided by the thumb member.

Alternatively or in addition, the worm may be disposed on the hand chassis. At least one of the motor, worm and the worm gear wheel may be disposed in a palmar region of the hand prosthesis.

Alternatively or in addition, the motor may be operable to rotate about a first axis and the worm may be operable to rotate about a second axis, the first and second axes being spaced apart from each other. The first and second axes may extend in substantially a same direction. Hence, the motor and worm may be disposed in relation to each other such that they occupy a less extended footprint. For example, the motor and worm may be disposed such that one of the motor and worm is above or behind the other.

Alternatively or in addition, the hand prosthesis may further comprise a coupling arrangement between the motor and the worm, the coupling arrangement being configured such that an axis of rotation of the worm differs from an axis of rotation of the motor. The coupling arrangement may be mechanically coupled to an output shaft of the motor and to an input shaft of the worm. The coupling arrangement may be configured to change a direction in which torque from the motor is applied to the worm.

More specifically, the coupling arrangement may comprise a gear arrangement. The gear arrangement may be configured to reduce a speed of rotation. For example, the gear arrangement may have a gearing ratio of substantially 4:1.

Alternatively or in addition, the hand prosthesis may further comprise a plurality of gear arrangements. The plurality of gear arrangements may be operative to reduce a speed of rotation. A first gear arrangement may form part of a coupling arrangement and a second gear arrangement may mechanically couple the coupling arrangement to the worm. The second gear arrangement may be a planetary gear arrangement. The second gear arrangement may, for example, have a gearing ratio of substantially 16:1.

Alternatively or in addition, the thumb member may be a thumb chassis. The thumb chassis may correspond to at least part of the metacarpal bone of the human hand, i.e. the bone that is located between the proximal phalange of the thumb and the carpus. Thus, the thumb chassis may be rotatable about an axis extending substantially along the length of the thumb chassis. The thumb chassis may be elongate in form.

Alternatively or in addition, the thumb chassis may be mechanically coupled to the hand chassis at a plurality of spaced apart locations. The thumb chassis may be coupled to the hand chassis at a first location towards a first end of the thumb chassis and towards a proximal end of the hand chassis. The worm and worm gear wheel may be disposed in the hand prosthesis towards the first location. The thumb chassis may be coupled to the hand chassis at a second location towards a second, opposing end of the thumb chassis and towards a distal end of the hand chassis.

The hand chassis may comprise a platform extending in a plane generally orthogonal of a plane in which finger members of the hand prosthesis lie when the finger members are fully extended. The hand chassis may comprise a bearing which is operative to provide for rotation of the thumb chassis in relation to the hand chassis, e.g. at the first location at which the thumb chassis is coupled to the hand chassis.

The hand chassis may further comprise a palmar chassis extending in a plane generally orthogonal to the plane of the platform. The palmar chassis may be configured for mounting of at least one digit member thereon. The palmar chassis may be configured to support components of the prosthetic hand, such as electronic assemblies operative to control the prosthetic hand.

The thumb chassis may be configured for attachment of a thumb assembly. Hence, the hand prosthesis may further comprise the thumb assembly. The thumb chassis may be configured for releasable attachment of the thumb assembly. The thumb assembly may comprise a thumb body. The thumb body may correspond to a natural thumb as defined by the phalanges of the natural thumb. The thumb body may comprise a cosmetic covering and may be configured such that the thumb body defines a shape that corresponds to the shape of a natural thumb. More specifically, the thumb assembly may be configured such that a central axis of the thumb body is spaced apart from a central axis of the thumb chassis. Hence, the thumb assembly may be configured such that at least one of a location on the thumb body and the central axis of the thumb body describes an arc as the thumb chassis rotates about its central axis. Thus, the thumb body may move closer to and away from a digit, such as a middle finger digit, as well as having its orientation in relation to the digit change.

Alternatively or in addition, the thumb assembly may comprise at least two articulated portions, with a pair of articulated portions being movable in relation to each other about a joint. Hence, a first joint may correspond to the metacarpophalangeal joint of the natural thumb. A second joint may correspond to the interphalangeal joint of the natural thumb.

More specifically, the thumb assembly may be configured for powered movement of the articulated portions in relation to each other. Hence, the hand prosthesis may comprise a further motor that is operable to provide for such powered movement. The further motor may be disposed on the thumb assembly in an arrangement of the kind described, for example, in WO 95/24875 or WO 2007/063266.

Alternatively or in addition, the hand prosthesis may comprise at least one finger member attached to the hand chassis. The finger member may be configured for powered movement of articulated portions of the finger member. Thus, the finger member may be a motor driven member of the kind described, for example, in WO 95/24875 or WO 2007/063266.

Alternatively or in addition, the thumb member may be rotatable about an axis extending away from a proximal end of the hand prosthesis. Thus, the axis may extend generally between the wrist and the finger tips when the fingers are extended.

Alternatively or in addition, the thumb member may be rotatable about an axis substantially parallel to a plane defined by a palm of the hand prosthesis.

Alternatively or in addition, the hand prosthesis may further comprise a position determining apparatus that is operative to determine a position of the thumb member. Hence, the position determining apparatus may be configured to determine the position of the thumb member in relation to the hand chassis.

More specifically, the position determining apparatus may comprise at least one position determining sensor that is operative to provide an electrical signal corresponding to a position of the thumb member. The electrical signal may be used for operative purposes, e.g. to indicate when the thumb member is at a fully open position or a fully closed position.

In a form, the position determining apparatus may comprise a plurality of switches, with each switch being operative when the thumb member is at a different position. For example, a first switch may be operative when the thumb member is at the fully open position and a second switch may be operative when the thumb member is at the fully closed position.

In another form, the position determining apparatus may comprise a rotary position sensor, such as a rotary potentiometer or a position encoder that uses an optical or magnetic sensing principle. Such a rotary position sensor may be configured to determine the position of the thumb member to a high degree of precision.

According to a second aspect of the present invention, there is provided a hand prosthesis comprising:
  a hand chassis;
  a thumb member mounted on the hand chassis for rotation of the thumb member in relation to the hand chassis about an axis;
  a motor disposed on one of the hand chassis and the thumb member, the motor being operable to drive a worm;
  a worm gear wheel disposed on the other of the hand chassis and the thumb member, the worm being in engagement with the worm gear wheel such that, upon operation of the motor, the thumb member rotates in relation to the hand chassis.

More specifically, the thumb member may be rotatable about an axis extending generally along the length of the thumb member.

According to a third aspect of the present invention, there is provided a hand prosthesis comprising:
  a hand chassis;
  a thumb chassis mounted on the hand chassis for rotation of the thumb chassis in relation to the hand chassis about an axis extending generally along the length of the thumb chassis;
  a motor disposed on one of the hand chassis and the thumb chassis, the motor being operable to drive a worm;
  a worm gear wheel disposed on the other of the hand chassis and the thumb chassis, the worm being in engagement with the worm gear wheel such that, upon operation of the motor, the thumb chassis rotates in relation to the hand chassis.

The thumb chassis may be configured for attachment of a thumb assembly. Hence, the hand prosthesis may further comprise the thumb assembly. The thumb chassis may be configured for releasable attachment of the thumb assembly. The thumb assembly may comprise a thumb body. The thumb body may correspond to a natural thumb as defined by the phalanges of the natural thumb. The thumb body may comprise a cosmetic covering and may be configured such that the thumb body defines a shape that corresponds to the shape of a natural thumb. More specifically, the thumb assembly may be configured such that a central axis of the thumb body is spaced apart from a central axis of the thumb chassis. Hence, the thumb assembly may be configured such that at least one of a location on the thumb body and the central axis of the thumb body describes an arc as the thumb chassis rotates about its central axis. Thus, the thumb body may move closer to and away from a digit, such as a middle finger digit, as well as having its orientation in relation to the digit change.

Alternatively or in addition, the thumb assembly may comprise at least two articulated portions, with a pair of articulated portions being movable in relation to each other about a joint. Hence, a first joint may correspond to the metacarpophalangeal joint of the natural thumb. A second joint may correspond to the interphalangeal joint of the natural thumb.

More specifically, the thumb assembly may be configured for powered movement of the articulated portions in relation to each other. Hence, the hand prosthesis may comprise a further motor that is operable to provide for such powered movement. The further motor may be disposed on the thumb assembly in an arrangement of the kind described, for example, in WO 95/24875 or WO 2007/063266.

Further embodiments of the second aspect of the present invention may comprise one or more features of the first aspect of the present invention.

BRIEF DESCRIPTION OF THE DRAWINGS

The present invention will now be described by way of example only with reference to the following drawings, of which:

FIG. 2 is a palm side view of core components of the prosthetic hand of FIG. 1 when the thumb chassis is in a first position;

FIG. 3 a thumb side view of core components of the prosthetic hand of FIG. 1 when the thumb chassis is in a first position;

FIG. 4 a palm side view of core components of the prosthetic hand of FIG. 1 when the thumb chassis is in a second position;

FIG. 5 is a thumb side view of core components of the prosthetic hand of FIG. 1 when the thumb chassis is in a second position;

SPECIFIC DESCRIPTION

Figure 1:
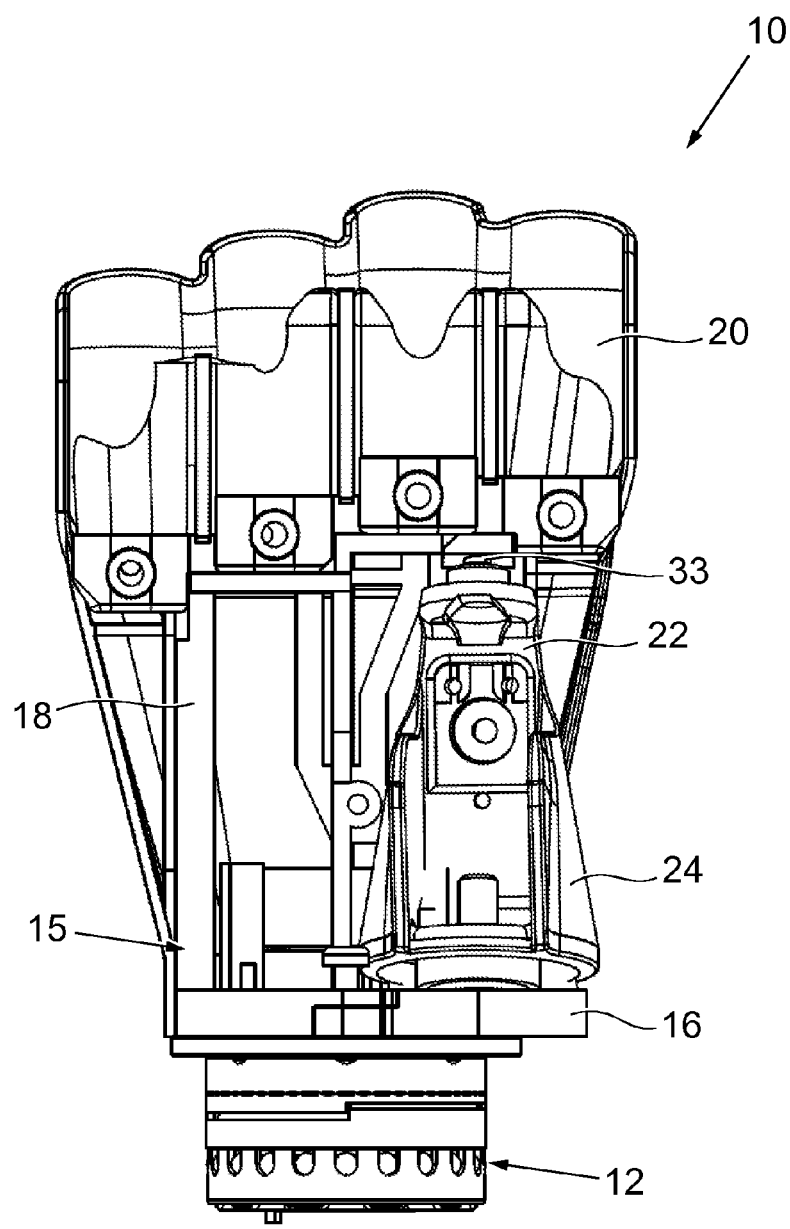
FIG. 1 is a palm side view of a prosthetic hand according to the present invention.
Figure 7:
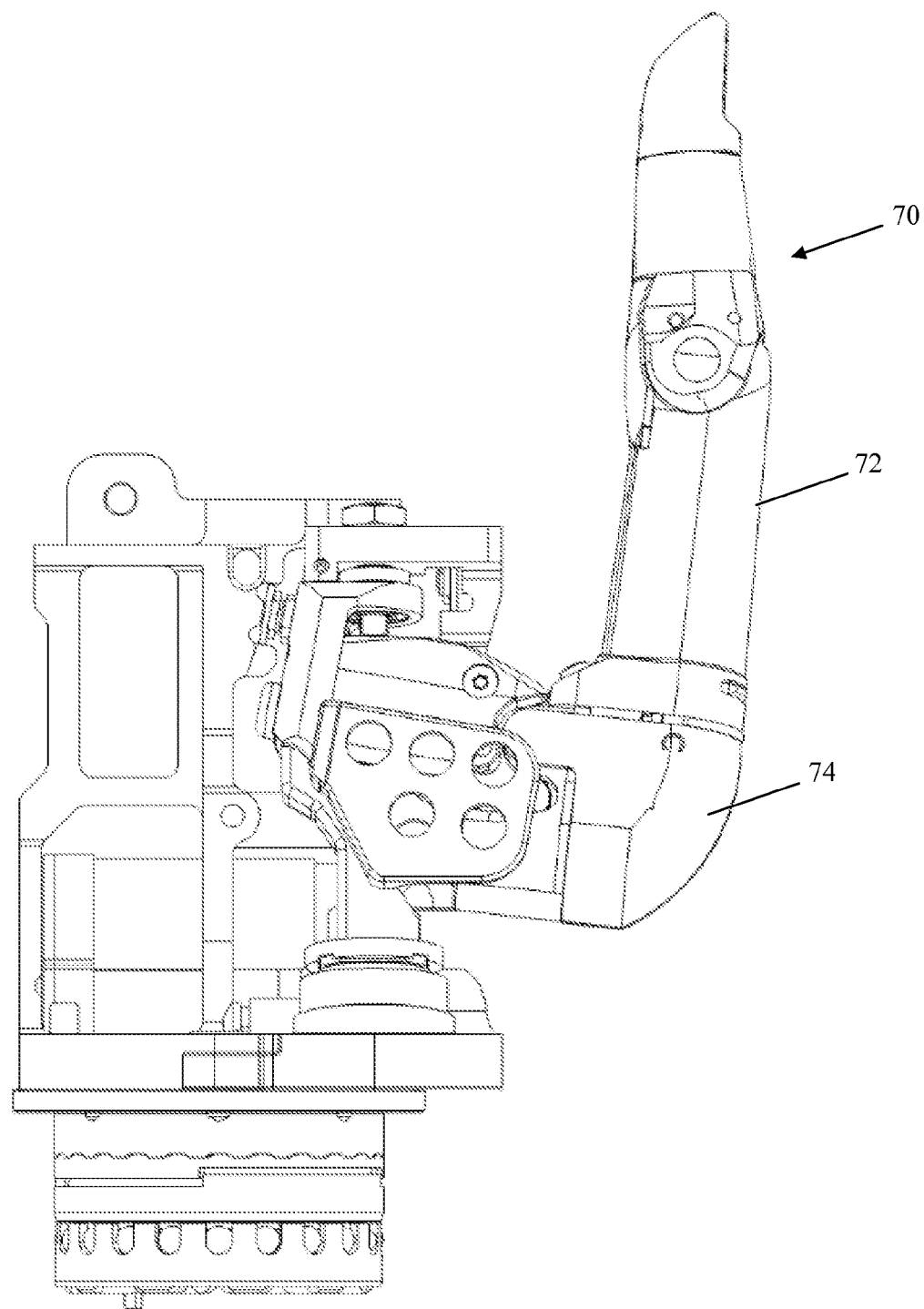
FIG. 7 is a thumb side view of the prosthetic hand of FIG. 1 with a thumb assembly attached thereto.
Figure 8:
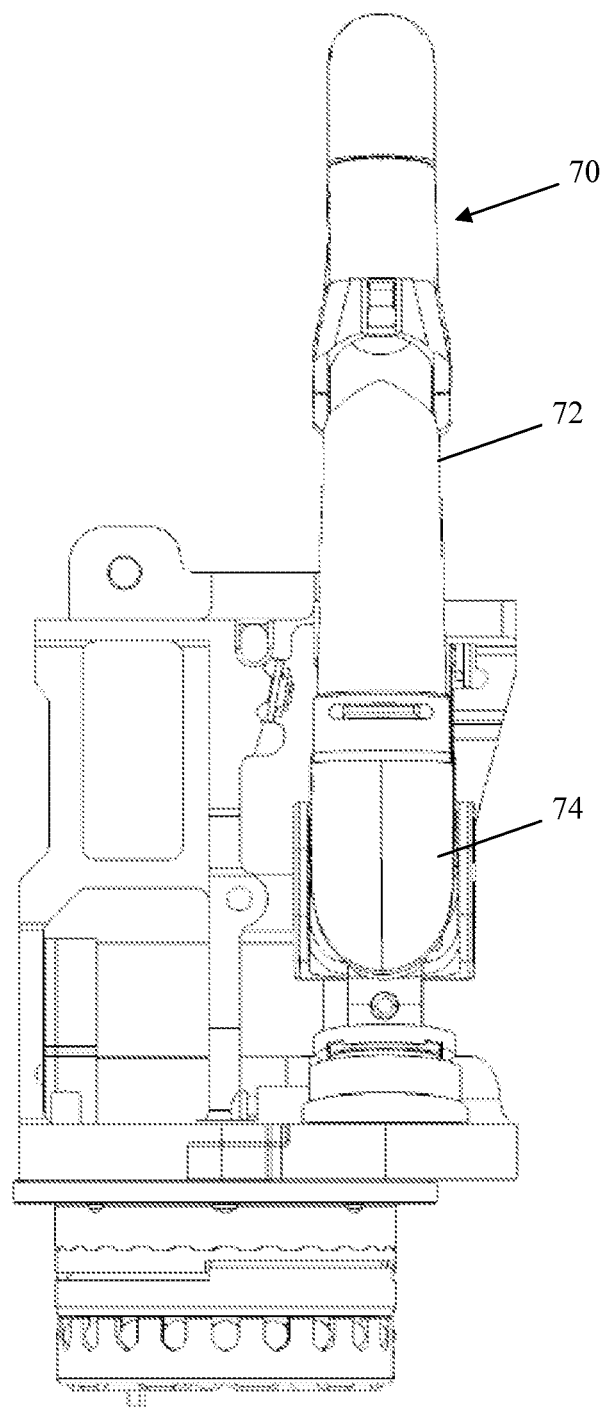
FIG. 8 is a palm side view of the prosthetic hand and thumb assembly of FIG. 7.

FIG. 1 shows a hand prosthesis 10, prosthetic hand 10, according to the present invention. The hand prosthesis 10 comprises a wrist connection arrangement 12, which is configured to connect to an arm stump (not shown). The wrist connection arrangement 12 is operable to provide for rotation of the prosthetic hand 10 in relation to the arm stump. The hand prosthesis 10 further comprises a hand chassis 15, which in turn comprises a platform 16 and a palmar chassis 18, which extends in a plane generally orthogonal to the platform 16. The platform 16 extends in a plane substantially orthogonal of a plane in which finger members (not shown) of the hand prosthesis 10 lie when the finger members are fully extended. The hand chassis 15 is configured for attachment of components of the prosthetic hand 10, such as electronic assemblies that are operative to control the prosthetic hand 10 and mechanical and electro-mechanical parts. More specifically, a fairing 20 is attached to the hand chassis 15 such that it defines a dorsal surface of the prosthetic hand 10 and a dorsal surface of the knuckle region of each of four finger digits (not shown) of the prosthetic hand 10. Each of the four finger digits is received in a space defined by the fairing 20 and is connected to a distal portion of the palmar chassis 18. Each of the four finger digits is of the kind described in WO 95/24875 or WO 2007/063266 such that it is configured for motor driven flexion and extension of articulated portions of the finger member. The hand prosthesis 10 further comprises a thumb chassis 22, which is described in more detail below. A thumb fairing 24 is attached to the thumb chassis 22. The thumb fairing 24 extends around the thumb chassis 22 and defines a space for reception of a thumb assembly 70, shown in FIGS. 7 and 8. When received in the defined space, the thumb assembly 70 is attached to the thumb chassis 22 and comprises a thumb body 72, which corresponds to a natural thumb as defined by the phalanges of the natural thumb. The thumb body 72 comprises articulated portions that are configured as is described in WO 95/24875 or WO 2007/063266 for motor driven flexion and extension using a thumb motor 74 positioned within the thumb assembly 70. The thumb assembly 70 is configured such that a central axis of the thumb body 72 is spaced apart from a central axis 30 of the thumb chassis 22. Hence and as will become apparent from the description below, the thumb assembly 70 is configured such that the central axis of the thumb body 72 describes an arc as the thumb chassis 22 rotates about its central axis 30.

FIGS. 2 and 3 show palm side and thumb side views respectively of core components of the prosthetic hand 10 of FIG. 1. Components in common with the hand prosthesis of FIG. 1 are designated with the same reference numerals. FIGS. 2 and 3 show the frame like structure of the palmar chassis 18 more clearly than FIG. 1. As can be seen from FIGS. 2 and 3, the thumb chassis 22 is elongate in form and mounted for rotation about its central axis 30 in relation to the palmar chassis 18 and the platform 16 by way of a rotational mounting 32 located on the platform 16. The rotational mounting 32 is described in more detail below. The thumb chassis 22 engages by means of a rotational coupling 33 at its distal end with a flange 34 defined by the palmar chassis 18. Hence, the thumb chassis 22 is supported on the hand chassis 15 towards opposing ends of the thumb chassis 22. As can be seen from FIG. 2, the thumb chassis 22 defines a thicker portion 36, which is shaped and configured for attachment of the thumb assembly described above with reference to FIG. 1. Although the thumb body is not shown in FIGS. 2 and 3 it will be appreciated that a central axis of the thumb body will lie parallel to the central axis 30 of the thumb chassis 22 and be further spaced apart from the dorsal surface of the prosthetic hand 10 than the central axis 30 of the thumb chassis 22. Hence, rotation of the thumb chassis 22 about its central axis 30 will cause the central axis of the thumb body to describe an arc. Consequently, the thumb body moves closer to and further away from a digit, such as a middle finger digit, as well as having its orientation in relation to the digit change. The position of the thumb chassis 22 is determined by means of first 38 and second 40 electrical switches. Each of the first 38 and second 40 electrical switches provides an electrical output 42 when the switch is closed. The first electrical switch 38 is disposed on the palmar chassis 18 such that the switch is operative when the thumb chassis 22 is in the fully closed position, i.e. when the thumb chassis 22 is turned fully anti-clockwise when the prosthetic hand 10 is viewed from the wrist connection arrangement 12. The second electrical switch 40 is disposed on the palmar chassis 18 such that the switch 40 is operative when the thumb chassis 22 is in the fully open position, i.e. when the thumb chassis 22 is turned fully clockwise when the prosthetic hand 10 is viewed from the wrist connection arrangement 12. Closure of each of the first and second switches 38, 40 is by means of a closure member borne by the thumb chassis 22.

FIGS. 4 and 5 show palm side and thumb side views respectively of the prosthetic hand 10 of FIGS. 2 and 3 after the thumb chassis 22 has rotated through ninety degrees such that the thicker portion 36 faces in the thumb side direction. Components in common with the hand prosthesis 10 of FIGS. 1 to 3 are designated with the same reference numerals. Hence, FIGS. 2 and 3 show a closed hand disposition, in which the thumb body (not shown) is closer to the middle finger, and FIGS. 4 and 5 show an open handed disposition, in which the thumb body (not shown) is further away from the middle finger. FIG. 4 shows an alternative position control sensing arrangement to that shown in FIG. 2. More specifically, the position of the thumb chassis 22 is determined by means of a rotary position sensor 44, such as a rotary potentiometer or a position encoder that uses an optical or magnetic sensing principle, which is operative to provide an electrical signal 46 corresponding to the position of the thumb chassis 22. Although shown schematically in FIG. 4, the rotary position sensor 44 is disposed at the upper end of the thumb chassis 22 such that a main body of the rotary position sensor 44 is attached to the flange 34 and a spindle of the rotary position sensor 44 is attached to the thumb chassis 22. In the embodiment of FIG. 4, a rotary position encoder that is operative according a magnetic principle of operation is used, namely Part Number HEM3-256-W from Dr. Fritz Faulhaber GmbH & Co. KG of Daimlerstr. 23, 71101 Schönaich, Germany.

Figure 6:
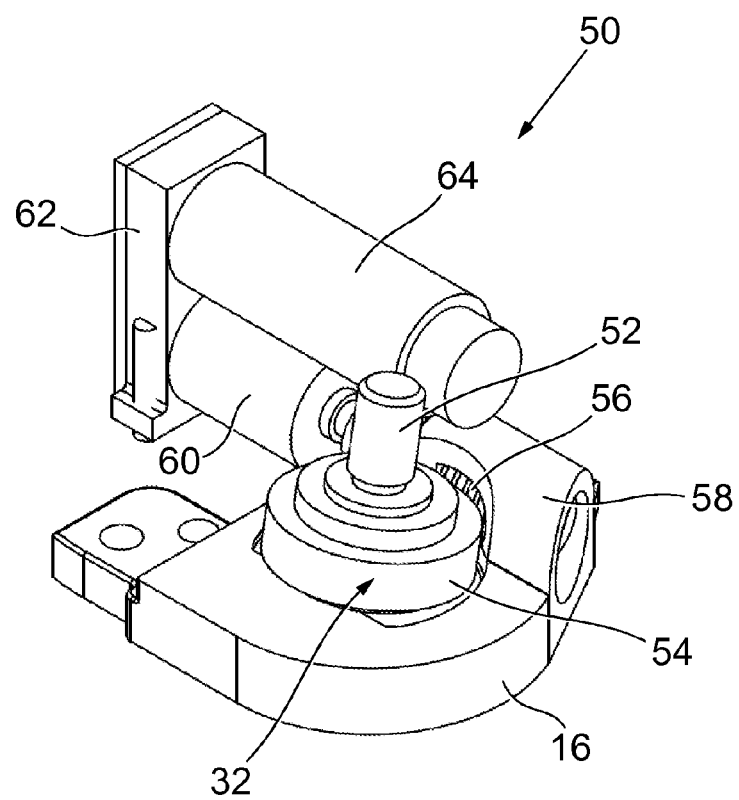
FIG. 6 is a perspective view of the drive mechanism of the prosthetic hand of FIG. 1.

The drive mechanism 50 for the thumb chassis 22 of FIGS. 1 to 5 is shown in FIG. 6. The rotational mounting 32 comprises an Oilite bearing (not shown), which is received in a recess formed in the platform 16, a spigot 52 of generally cylindrical form, which is mounted on the Oilite bearing, and a worm gear wheel 54, which is mounted on the spigot 52 such that the upper end of the spigot 52 extends beyond the worm gear wheel 54. The thumb chassis 22 of FIGS. 1 to 5 is mounted on the upper end of the spigot 52. In use, the spigot 52, the worm gear wheel 54 and the thumb chassis 22 rotate together on the Oilite bearing. A worm 56 is supported in a housing 58 attached to the platform 16 such that the worm 56 is located behind (i.e. further away from the palmar region than) the rotational mounting 32 and such that teeth (not shown) formed on the outer surface of the worm gear wheel 54 mesh with the thread of the worm 56. A shaft extending from the worm 56 in a direction generally parallel to a plane defined by the palmar region of the prosthetic hand 10 connects to a planetary gearhead 60 having a 16:1 gearing ratio. The planetary gearhead 60 is a Series 10/1 planetary gearhead from Dr. Fritz Faulhaber GmbH & Co. KG of Daimlerstr. 23, 71101 Schönaich, Germany. The planetary gearhead 60 connects to a gearbox 62 having a 4:1 gearing ratio, which is configured to change a drive direction and which in turn connects to a motor 64, which is located above the in-line disposition of planetary gearhead 60 and worm 56. The motor 64 is a Series 1024 coreless DC micro-motor from Dr. Fritz Faulhaber GmbH & Co. KG of Daimlerstr. 23, 71101 Schönaich, Germany. Hence, in use, the motor 64 is operative to drive the gearbox 62, which in turn drives the planetary gearhead 62, which drives the worm 56 to thereby cause rotation of the worm gear wheel 54 and hence the rotational mounting 32. In combination the planetary gearhead 62 and the gearbox effect a 64:1 reduction in the rotational speed of the motor 64.

Although the determination of the position of the thumb chassis 22 has been described above as being performed by means of first 38 and second 40 electrical switches, or rotary position sensor 44, it should be appreciated that the position of the thumb chassis 22 may additionally or alternatively be determined by electronically monitoring the "stall out" of the motor 64. That is, the position of the thumb chassis 22 may be determined by monitoring the drive current of the motor 64. Typically, when the thumb chassis 22 reaches a stop position the current of the motor increases. The drive current of the motor 64 is monitored, and if the drive current increases for a given period of time (e.g. around a few milliseconds) the motor is stopped and a signal is given that the thumb chassis 22 has reached its end position. The monitoring of the motor drive current is typically performed by control software associated with the prosthesis 10.

The invention claimed is:

1. A hand prosthesis comprising:
a hand chassis;
a thumb chassis mounted on the hand chassis for rotation of the thumb chassis in relation to the hand chassis about an axis extending generally along the length of the thumb chassis;
a thumb chassis motor disposed on the hand chassis, the thumb chassis motor being operable to drive a worm;
a worm gear wheel disposed on the thumb chassis, the worm being in engagement with the worm gear wheel such that, upon operation of the thumb chassis motor, the thumb chassis rotates in relation to the hand chassis; and
a thumb assembly,
wherein the thumb assembly attaches to the thumb chassis, the thumb assembly having a thumb motor positioned within the thumb assembly such that the thumb assembly moves at an angle to the hand chassis independently of the movement of the thumb chassis.

2. A hand prosthesis according to claim 1, in which the worm gear wheel is disposed towards a proximal end of the thumb chassis.

3. A hand prosthesis according to claim 1, in which the thumb chassis motor is operable to rotate about a first axis and the worm is operable to rotate about a second axis, the first and second axes being spaced apart from each other.

4. A hand prosthesis according to claim 3, in which the first and second axes extend in substantially a same direction.

5. A hand prosthesis according to claim 1, in which the hand prosthesis further comprises a coupling arrangement between the thumb chassis motor and the worm, the coupling arrangement being configured such that an axis of rotation of the worm differs from an axis of rotation of the thumb chassis motor.

6. A hand prosthesis according to claim 5, in which the coupling arrangement comprises a gear arrangement configured to reduce a speed of rotation.

7. A hand prosthesis according to claim 5, in which the hand prosthesis further comprises a plurality of gear arrangements, with a first gear arrangement forming part of the coupling arrangement and a second gear arrangement mechanically coupling the coupling arrangement to the worm.

8. A hand prosthesis according to claim 7, in which the second gear arrangement is a planetary gear arrangement.

9. A hand prosthesis according to claim 1, in which the thumb chassis is mechanically coupled to the hand chassis at a plurality of spaced apart locations.

10. A hand prosthesis according to claim 1, in which the hand chassis comprises a platform extending in a plane generally orthogonal of a plane in which finger members of the hand prosthesis lie when the finger members are fully extended.

11. A hand prosthesis according to claim 10, in which the hand chassis further comprises a palmar chassis extending in a plane generally orthogonal to the plane of the platform, the palmar chassis being configured for mounting of at least one digit member thereon.

12. A hand prosthesis according to claim 1, in which the hand chassis comprises a bearing that is operative to provide for rotation of the thumb chassis in relation to the hand chassis.

13. A hand prosthesis according to claim 1, in which the thumb assembly comprises at least two articulated portions, with a pair of articulated portions being movable in relation to each other about a joint.

14. A hand prosthesis according to claim 1, in which the hand prosthesis further comprises at least one finger member attached to the hand chassis, with the finger member being configured for powered movement of articulated portions of the finger member.

15. A hand prosthesis according to claim 1, in which the thumb chassis is rotatable about an axis extending away from a proximal end of the hand prosthesis.

16. A hand prosthesis according to claim 1, in which the thumb chassis is rotatable about an axis substantially parallel to a plane defined by a palm of the hand prosthesis.

17. A hand prosthesis according to claim 1, in which the hand prosthesis further comprises a position determining apparatus that is operative to determine a position of the thumb chassis.

18. A hand prosthesis according to claim 17, in which the position determining apparatus comprises at least one position determining sensor that is operative to provide an electrical signal corresponding to a position of the thumb chassis.

19. A hand prosthesis according to claim 17, in which the position determining apparatus comprises a plurality of switches, with each switch being operative when the thumb chassis is at a different position.

20. A hand prosthesis according to claim 17, in which the position determining apparatus comprises a rotary position sensor.

* * * * *